US00PP15044P2

(12) United States Plant Patent
Olesen et al.

(10) Patent No.: US PP15,044 P2
(45) Date of Patent: Jul. 27, 2004

(54) MINIATURE ROSE PLANT NAMED 'POULHI013'

(50) Latin Name: *Rosa hybrida*
Varietal Denomination: POULhi013

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/672,350

(22) Filed: Sep. 25, 2003

(51) Int. Cl.[7] ..... A01H 5/00
(52) U.S. Cl. ..... Plt./119
(58) Field of Search ..... Plt./119

*Primary Examiner*—Bruce R. Campell
*Assistant Examiner*—Susan B. McCormick-Ewoldt

(57) ABSTRACT

A new miniature rose plant which has abundant, orange flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi013'.

SUMMARY OF THE INVENTION

The present invention constitutes a new and distinct variety of miniature rose plant which originated from a controlled crossing between the female parent Mandy Kordana, non-patented, and the male parent 'KORkelvia' described and illustrated in U.S. Plant Pat. No. 11,232 issued on Feb. 22, 2000. The two parents were crossed and the resulting seeds were planted in a controlled environment. The new variety is named 'POULhi013'.

The new rose may be distinguished from its seed parent, Mandy Kordana, by the following combination of characteristics:

1. Whereas the general tonality of Mandy Kordana is Red Group 40A, 'POULhi013' is Red Group 33B.
2. Whereas Mandy Kordana has a tall growth habit, 'POULhi013' has a very compact growth habit.

The new variety may be distinguished from its pollen parent, 'KORklevia' by the following combination of characteristics:

1. 'KORklevia' has 25 to 30 petals, where 'POULhi013' has 60 to 70 petals.
2. Upper surface of interior petals on 'KORklevia' are Yellow Group 16C while the same on 'POULhi013' are Orange-Red Group 33B.
3. Bud color is Orange-White Group 159C on 'KORklevia' while Red Group 41A on 'POULhi013'.

The objective of the hybridization of this rose variety for commercial culture was to create a new and distinct variety with unique qualities, such as:

1. Uniform and abundant orange flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi013' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi013' was selected by the inventors as a single plant from the progeny of the hybridization work done in June 1998.

Asexual reproduction of 'POULhi013' by cuttings and traditional budding was first done by L. Pernille and Mogens N. Olesen in their nursery in Fredensborg, Denmark in July 1999. This initial and other subsequent propagations conducted in controlled environments have demonstrated that the characteristics of 'POULhi013' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi013'. Specifically illustrated in FIG. 1:

FIG. 1.1; Stem showing branching and the attachment of leaves, buds, peduncle and open flower;

FIG. 1.2; Flower bud, partially opened bud, and open bloom;

FIG. 1.3; Flower petals, detached;

FIG. 1.4; Sepals, receptacle, and pedicel;

FIG. 1.5; Juvenile growth exhibiting Anthocyanin, juvenile flower bud and leaves and mature leaves.

FIG. 1.6; Bare stem exhibiting thorn.

DETAILED DESCRIPTION OF THE VARIETY

The following is a description of 'POULhi013', as observed in its growth in glasshouse in Burlington, Canada in 15 cm diameter pots. Observed plants are 10 weeks of age. Color references are made using The Royal Horticultural Society (London, England) Colour Chart, 1995, except where common terms of color are used.

For a comparison, several physical characteristics of the rose variety 'POULobe', a rose variety from the same inventors described and illustrated in U.S. Plant Pat. No. 10,728 issued on Dec. 22, 1998, are compared to 'POULhi013' in Chart 1.

CHART 1

| | 'POULhi013' | 'POULobe' |
|---|---|---|
| Petal Count | 60 to 70 petals. | 35 to 40 petals. |
| Petal Color, upper side of outer petals. | Red Group 41B to Orange Red Group 33B to 33D. | Reg Group 44B. |
| Filament color | Yellow Group 6A | Pale Green to White |

FLOWER AND FLOWER BUD

Blooming habit: Continuous.

Flower bud:

*Size.*—Upon opening, 20 mm–22 mm in length from base of receptacle to end of bud. Bud diameter is 12 mm.

*Bud form.*—Pointed ovoid.

*Bud color.*—As sepals unfold, Red Group 41A. At ¼ opening, Red Group 43B.

*Sepals.*—Yellow Green Group 146B in color. Weak foliaceous appendages on three of the five sepals. Surfaces of sepals are weakly pubescent. Stipitate glands are scant in quantity. Shape: Sepal apex is cirrose. Base is flat at union with receptacle. Size: 32 mm long×7 mm wide.

*Receptacle.*—Surface: Pubescent. Shape: Funnel to Urn-Shaped. Size: 6 mm (h)×6 mm (w). Color: Yellow Green Group 144A.

*Peduncle.*—Surface: Stipitate glands present in medium quantity. Surface is lightly pubescent. Length: 55 to 60 mm average length. Color: Yellow Green Group 144A. No anthocyanin observed. Strength: Rigid.

*Borne.*—Singly.

Flower bloom:

*Fragrance.*—Light floral fragrance.

*Duration.*—As a pot plant, flowers last from 10 to 13 days.

*Size.*—Average flower diameter is 40 mm when open. Flower depth is 25 mm.

*Form.*—Shape of flower when viewed from the side: Upon opening, upper part: Flat. Upon opening, lower part: Flattened convex. Open flower, upper part: Flat. Open flower, lower part: Flattened convex.

*Petalage.*—Average range: 60 to 70 petals under normal conditions with 12 petaloids.

Color:

*Upon opening, petals.*—Outermost petals: Outer Side is Red Group 39A at the marginal and middle petal zones, with intonations of Red Group 35C at the middle zone. Inner Side is Red Group 41B with intonations of Red Group 41C streaking from the basal zone in a radial pattern. Innermost petals: Outer Side is Red Group 39A to Red Group 40A with intonations of Red Group 35C at the middle zone. Inner Side is Orange Red Group 33B with light intonations of Red Group 33C at the middle zone.

*Upon opening, basal petal spots.*—Outermost petals: Outer Side is Yellow Group 4C. Inner Side is Yellow Group 4A. Innermost petals: Outer Side is Yellow Group 4A to 4C. Inner Side is Yellow Group 4B to 5B.

*After opening, petals.*—Outermost petals: Outer Side is Red Group 39A to 41A with intonations of Red 39B to 39C. Inner Side: Red Group 41B to Orange-Red Group 33B with intonations of Orange-Red Group 33D. Innermost petals: Outer Side is Red Group 39A to 41A with intonations of Red 39B to 39C. Inner Side: Red Group 41B to Orange-Red Group 33B with intonations of Orange-Red Group 33D.

*After opening, basal petal spots.*—Outermost petals: Outer Side is Yellow Group 4A to 4C. Inner Side is Yellow Group 4A. Innermost petals: Outer Side is Yellow Group 4A to 4C. Inner Side is Yellow Group 4A.

General tonality: On open flower the general tonality is Orange-Red Group 33B. No change in the general tonality observed after the flower has aged.

Petals:

*Petal reflex.*—Petals reflex slightly.

*Petal edge.*—Entire.

*Shape.*—The apex is round with a point at the center. The base is Acute.

*Size.*—28 mm in length by 28 mm wide.

*Petaloids.*—Quantity: 10 to 15 average. Size: 15 mm long; 5 mm wide. Color: Outer Side is Red Group 39A to 41A with intonations of Red 39B to 39C. Inner Side: Red Group 41B to Orange-Red Group 33B with intonations of Orange-Red Group 33D.

*Thickness.*—Petals are of thick substance.

*Texture.*—Smooth.

*Arrangement.*—Formal.

Reproductive organs:

*Pistils.*—Length: 8 mm long. Quantity: 25.

*Pollen.*—None observed.

*Anthers.*—Size: 2 mm long. Color: Yellow Group 6A. Quantity: 38.

*Filaments.*—Color: Yellow Group 6A. Length: 5 mm.

*Stigmas.*—Slightly superior in location to anthers. Color: Greyed-Orange Group 168D.

*Styles.*—Color: Yellow Green Group 149D with intonations of Red Group 39A.

*Seed formation.*—Seeds not observed due to the method of culture.

PLANT

Plant growth: Vigorous, compact, upright to bushy. When grown as a 12–15 cm pot plant, the average height of the plant itself is 25 cm and the average width is 18 cm.

Stems:

*Color.*—Young wood: Yellow Green Group 146A. Older wood: Yellow Green Group 146A. Internodal Distance: 40 mm.

*Surface.*—Young wood: Smooth. Older wood: Smooth.

*Prickles.*—Incidence: 5 per 10 cm of stem. Size: Average length: 5 mm. Color: Greyed-Yellow Group 160C. Shape: Linear.

Plant foliage: Normal number of leaflets on normal leaves in middle of the stem: 7 leaflets.

*Compound leaf size.*— 95 mm (l)×70 mm (w).

*Quantity.*—Each stem exhibits an average occurrence of 7 compound leaves.

*Color*.—Mature foliage: Upper Leaf Surface: Green Group 137A. Lower Leaf Surface: Green Group 138B. Juvenile foliage: Upper Leaf Surface: Green Group 139A. Lower Leaf Surface: Green Group 138B. Anthocyanin intonation: Location: On plants grown under high light conditions, leaf margins on developing leaves may exhibit intonations of Greyed-Purple Group 183A.

Plant leaves and leaflets:

*Stipules*.—Size: 7 mm in length. Color: Green Group 137B. Stipitate glands: Present in medium quantity.

*Petiole*.—Length: 18 mm. Color: Yellow-Green Group 144A. Underneath: Prickles, stipitate glands, and pubescense are characteristic.

*Rachis*.—Length: 30 mm. Color: Yellow-Green Group 144A. Underneath: Prickles, stipitate glands, and pubescense are characteristic. Anthocyanin: Greyed-Purple Group 183A where leaf attaches to the stem.

*Leaflet*.—Size of terminal leaflet: 43 mm long×30 mm wide. Edge: Serrated. Shape: Base is rounded. Apex is acute. Texture: Smooth. Arrangement: Odd pinnate. Venation: Reticulate. Leaf Gloss: Matte finish.

Disease resistance:

Average resistance to mildew, black spot, and Botrytis under normal growing conditions in Burlington, Canada.

What is claimed is:

1. A new and distinct variety of rose plant of the miniature class, substantially as herein illustrated and described as a distinct and novel rose variety due to its abundant, orange flowers, vigorous growth, compact habit, suitability for production from softwood cuttings in pots, and durable flowers and foliage which make the variety suitable for distribution in the floral industry.

* * * * *

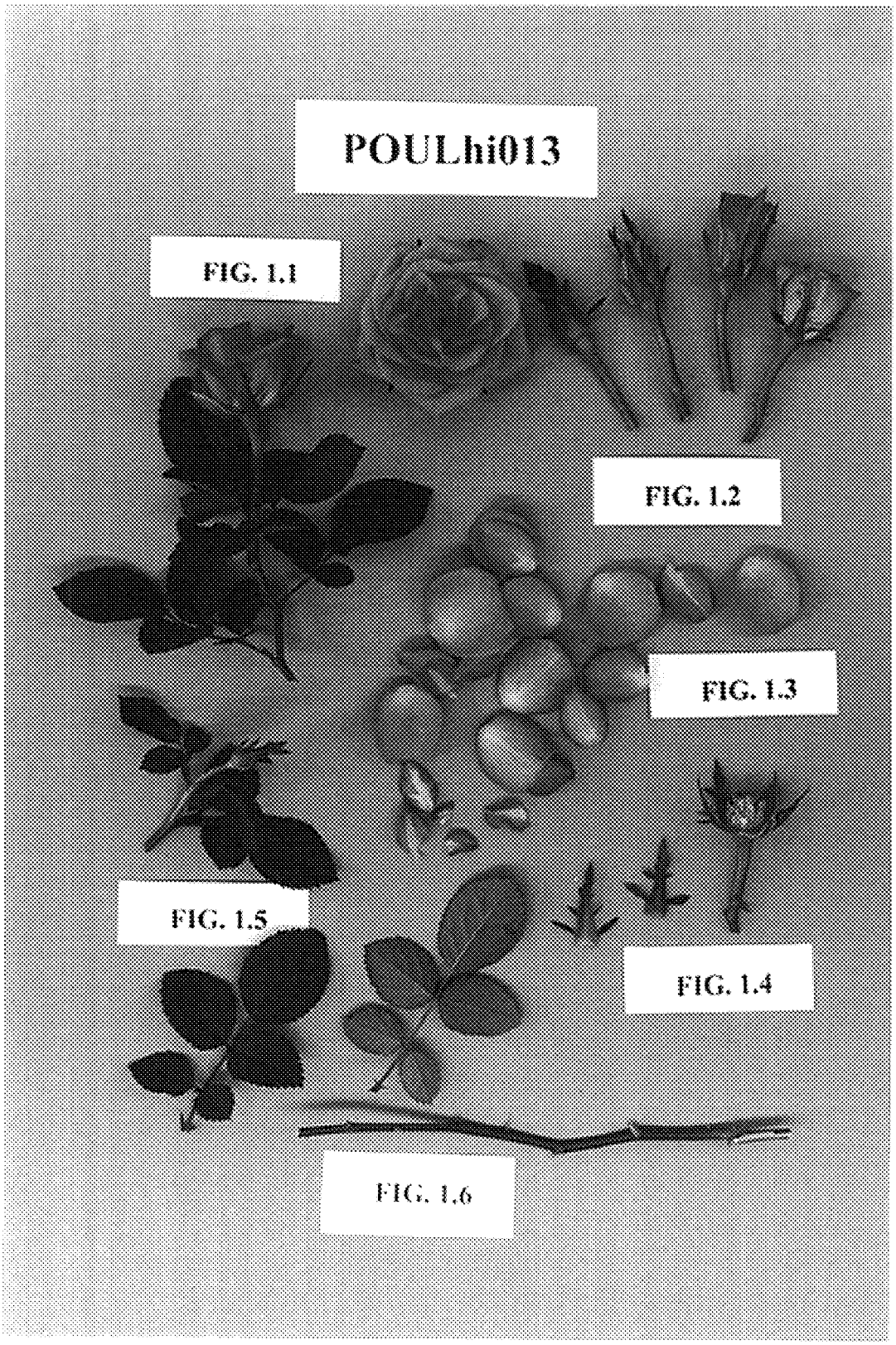
POULhi013
FIG. 1.1
FIG. 1.2
FIG. 1.3
FIG. 1.5
FIG. 1.4
FIG. 1.6